United States Patent
Brayer et al.

Patent Number: 5,198,571
Date of Patent: Mar. 30, 1993

[54] MONOFUNCTIONALIZATION OF PHENOLIC HYDROXY ONTO A POLYPHENOL

[75] Inventors: Jean-Louis Brayer, Le Haudoin; Daniel Calvo, Romainville; François Ottello, Livry Gargan, all of France

[73] Assignee: Roussel Uclaf, Paris, France

[21] Appl. No.: 807,982

[22] Filed: Dec. 16, 1991

[30] Foreign Application Priority Data

Dec. 18, 1990 [FR] France .................. 90 15810

[51] Int. Cl.$^5$ ............................ C07C 69/88
[52] U.S. Cl. ........................ 560/70; 560/67; 560/14; 560/64; 560/21; 560/66; 562/476; 568/433; 568/763; 568/651; 558/423; 558/56; 556/437
[58] Field of Search ............ 560/67, 70, 66, 64; 562/476; 568/433, 763, 651; 558/423

[56] References Cited

FOREIGN PATENT DOCUMENTS 1566626 5/1969 France .

OTHER PUBLICATIONS

Scheline, R. R. Acta Chemic. Scand. vol. 20 No. 4 p. 1182 1966 CA91:123715y 1979.

*Primary Examiner*—Paul J. Killos
*Attorney, Agent, or Firm*—Bierman and Muserlian

[57] ABSTRACT

A region-specific monofunctionalization of a phenolic hydroxy onto a polyphenol for the preparation of a compound of the formula

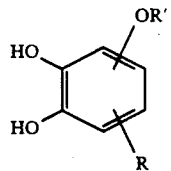

wherein R is selected from the group consisting of hydrogen, alkyl of 1 to 8 carbon atoms, alkenyl and alkynyl of 2 to 8 carbon atoms, —CN, formyl, carboxy, alkoxy carbonyl of up to 9 carbon atoms, aralkoxy carbonyl or up to 12 carbon atoms and halogen and R' is a hydroxy protective group comprising reacting a polyphenol of the formula

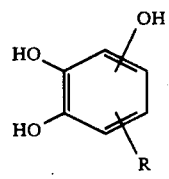

wherein R has the above definition with a base to form the corresponding dianion, reacting the latter with a trialkyl borate of the formula

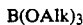

wherein Alk is alkyl of 1 to 6 carbon atoms to form a compound of the formula

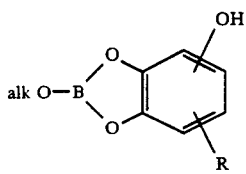

reacting the latter with a reagent capable of introducing a hydroxy protective group and reacting the latter with a hydrolysis agent for the oxygen-boron bond to obtain the corresponding compound of Formula I.

9 Claims, No Drawings

MONOFUNCTIONALIZATION OF PHENOLIC HYDROXY ONTO A POLYPHENOL

STATE OF THE ART

Rated prior art includes French Patent No. 1,566,626 and Acta. Chemica-Scandinavica, Vol. 20, No. 4 (1966), p. 1182, Chem. Abs., Vol. 46, No. 9, (1952) (4004b and e) and Chem. Abs., Vol. 91, No. 15 (1979), p.608 (123,715 g).

OBJECTS OF THE INVENTION

It is an object of the invention to provide a novel process for the preparation of the compounds of Formula I.

This and other objects and advantages of the invention will become obvious from the following detailed description.

THE INVENTION

The novel process of the invention for the preparation of a compound of the formula

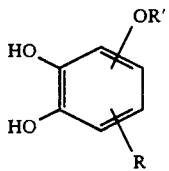

I wherein R is selected from the group consisting of hydrogen, alkyl of 1 to 8 carbon atoms, alkenyl and alkynyl of 2 to 8 carbon atoms, —CN, formyl, carboxy, alkoxy carbonyl of up to 9 carbon atoms, aralkoxy carbonyl of up to 12 carbon atoms and halogen and R' is a hydroxy protective group comprises reacting a polyphenol of the formula

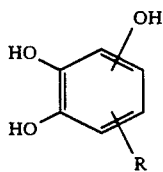

II wherein R has the above definition with a base to form the corresponding dianion, reacting the latter with a trialkyl borate of the formula

B(OAlk)$_3$ wherein Alk is alkyl of 1 to 6 carbon atoms to form a compound of

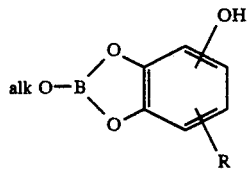

III reacting the latter with a reagent capable of introducing a hydroxy protective group and reacting the latter with a hydrolysis agent for the oxygen-boron bond to obtain the corresponding compound of Formula I.

Examples of R are alkyl such as methyl, ethyl, propyl, isopropyl and branched or linear butyl, pentyl and hexyl; alkenyl such as vinyl, allyl, isopropenyl, 2-methyl-allyl and isobutenyl; alkynyl such as ethynyl, propargyl, butynyl and pentynyl; alkoxy carbonyl such as methoxy carbonyl, ethoxycarbonyl, propoxycarbonyl, isopropoxycarbonyl, butoxycarbonyl, isobutoxycarbonyl and tert-butoxycarbonyl; aralkoxy carbonyl such as benzyloxycarbonyl; and halogen such as fluorine, chlorine, bromine and iodine.

The hydroxy protective groups may be any known protective groups such as those described in "Protective Groups in Organic Synthesis" by Green (John Wiley and Sons). Examples of such groups are primary and secondary alkyl such as methyl, ethyl and isopropyl; alkanoyl such as pivaloyl, optionally substituted aryl such as phenyl and nitrophenyl; aralkyl such as benzyl and phenethyl; arylsulfonyl such as p-toluene sulphonyl; aryl silyl or alkylaryl silyl such as diphenyl tert-butyl silyl.

In a preferred mode of the process of the invention, the compound of Formula II is reacted with at least two equivalents of a base, preferably sodium hydride or an organometal compatible with R, preferably a lithium alkyl and the blocking reaction with the borate which is preferably trimethyl, triethyl, tripropyl, triisopropyl or tributyl borate is effected in an anhydrous aprotic organic solvent such as tetrahydrofuran or dimethylformamide. The reactions are preferably effected at room temperature without isolation of intermediates. The reagent for the hydroxy protective forming groups is preferably a halide and the hydrolysis agent is an acid such as hydrochloric acid or an oxidizing agent such as hydrogen peroxide.

The structure of the intermediate cyclic borate of Formula III does not effect the mechanism of the blocking action with trialkyl borate. However, it is likely that in situ other intermediates may be present due to equilibrium conditions such as a boronate of the formula

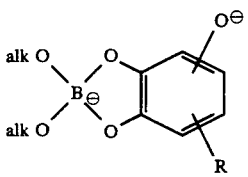

IV

It can also be possible that the intermediate having a protected hydroxy resulting from the boronate of Formula IV could have the formula

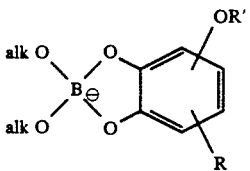

V

Processes for the preparation of compounds of Formula I have been described in the art, some of which used a boron derivative. The process described by Scheline (Acta. Scand., Vol. 20 (1966), No. 4, p. 1182) and resumed by Kato (Synth. Commun. (1980) - p. 172) achieves the blocking of two 1,2-hydroxy's using sodium borate. Also it can be noted that generally blocking of diols by derivatives of boric acid has been described, notably in the chemistry of sugars. These blockings use particularly derivatives of boric acid of the formula A—B(OH)$_2$, in which A is aryl or polystyryl (Frechet et al, J. Am. Chem. Soc., Vol. 101, (1979), p. 432).

The process of the present invention has important advantages compared to the those described in the literature. It uses inexpensive commercial reagents which are very easy to manipulate, it does not require isolation of any intermediates and gives excellent yields, and above all, it is very general due to the fact that it avoids the use of conditions which are both basic and aqueous.

The use of such conditions limits the processes of the prior art for the preparation of compounds of Formula I in which R' is lower alkyl, preferably methyl. The use of aqueous conditions in these processes does not permit the use of protection reagents which are unstable or which react too slowly on the phenol under these conditions. The preparation of products in which the protected hydroxy is unstable under these conditions is not allowed. Moreover, the process of the present invention offers the advantage of preserving the integrity of the R, which is not the case with processes of the prior art.

The products of Formula I are products which are very useful in organic synthesis, notably because of the presence of the R group, starting from which homologation reactions in particular are possible. However, substitutions on the ring are also possible. Among the uses described, there can be mentioned alkaloid syntheses of cotarnine type and, more generally, syntheses using gallic acid at the start, analogues or derivatives (see for example, Kapadia et al, J. Pharm. Sci. Vol. 58, No. 9 (1969), p. 1157, or Takuma et al, Mitsubishi Chemical. "An efficient synthesis of cotarnine" Congres IUPAC de Kyoto 29/05-03/06/1988 or also Y. Kato. Synth. Comm. Vol. 172, (1980)).

In the following examples, there are described several preferred embodiments to illustrate the invention. However, it should be understood that the invention is not intended to be limited to the specific embodiments.

EXAMPLE 1

Methyl 3-[(4-methyl-phenyl)-sulfonyloxy]-4,5-dihydroxy benzoate 1 g of methyl gallate was introduced under an inert gas atmosphere into 30 ml of anhydrous dimethylformamide and then 0.492 g of sodium hydride suspended as 53% in oil were added slowly. The mixture was stirred at ambient temperature for one hour and then 9.953 ml of triethyl borate were added. The mixture was stirred for 2 hours at ambient temperature and then, after standing for 15 hours, the mixture was poured into a mixture of ice-cooled water and N hydrochloric acid (pH approx. 3). The crystals were separated, rinsed with water and dried under reduced pressure to obtain 1.78 g of crude expected product which was washed with isopropyl ether to obtain 1.66 g of the expected product (Yield: 90.4%).

| NMR Spectrum - (CDCl$_3$ - 60 MHz) | |
|---|---|
| Hydroxy H | 3 ppm |
| Aromatic H's | from 7.05 to 7.9 ppm |
| Methyl H of the ester | 3.86 ppm |
| Methyl H in the position 4 of the phenyl | 2.5 ppm |

EXAMPLE 2

Methyl 3-[(4-methyl-phenyl)-sulfonyloxy]-4,5-dihydroxy benzoate 1 liter of anhydrous tetrahydrofuran was placed under an inert gas atmosphere and 118 g of sodium hydride in suspension in oil were added with stirring at ambient temperature. Then 555 ml of triethyl borate were added over 15 minutes followed by adding 379 g of methyl gallate in 1.8 liter of tetrahydrofuran over 2 hours. The mixture was stirred for 15 hours and then 283 g of anhydrous potassium carbonate were added. A solution of 410 g of tosyl chloride in 820 ml of tetrahydrofuran was added over 30 minutes and the mixture was stirred for 24 hours, then for 2 hours at reflux, followed by cooling and pouring into an ice - N hydrochloric acid (2 liters) mixture. Extraction took place with ethyl acetate, the organic phase was washed with water saturated with sodium chloride, dried and the solvent was evaporated off. The residue was impasted in isopropyl ether, then in methylene chloride and after separating and drying, 576 g of the expected product were obtained with a melting point of 196° C. (Yield 89.8%) identical to that obtained in Example 1.

EXAMPLE 3

Propyl 3-[(4-methyl-phenyl)-sulfonyloxy]-4,5-dihydroxy benzoate 400 ml of anhydrous tetrahydrofuran were placed under an inert gas atmosphere and 62 g of sodium hydride in suspension in oil were added and 294 ml of triethyl borate were added over 5 minutes with stirring. Then, a solution of 230 g of propyl gallate in 600 ml of tetrahydrofuran was added over 2 hours 45 minutes at 15° C. and the mixture was stirred at 18° C. for 2 hours. Then, a solution of 217 g of tosyl chloride in 500 ml of tetrahydrofuran was added and 70 g of potassium carbonate were added. The mixture was stirred for 17 hours at ambient temperature and then was refluxed. Another 70 g of potassium carbonate were added, followed by cooling, pouring into a mixture of ice and 400 ml of 22° Be hydrochloric acid, saturating with sodium chloride and extracting with ethyl acetate. The organic phase was dried and the solvent was evaporated off. The residue was impasted in methylene chloride and dried to obtain 324.6 g of the expected product melting at 152° C. (Yield: 81.7%).

EXAMPLE 4

Methyl 3-(benzyloxy)-4,5-dihydroxy benzoate 1 g of methyl gallate and 30 ml of anhydrous dimethylformamide were mixed together under an inert gas atmosphere and then 0.49 g of sodium hydride in suspension at 53% in oil were added at 15° C. After one hour, 0.606 ml of trimethyl borate were added at ambient temperature and a solution of 0.645 ml of benzyl bromide in 10 ml of dimethylformamide was added over one hour. The mixture was stirred at ambient temperature for 3 hours and then was poured into a mixture of water, ice and 10 ml of 2N hydrochloric acid. Extraction took place with ethyl acetate. The organic phase was dried and brought to dryness. The residue was taken up in an ethyl ether - isopropyl ether mixture and the crystals were filtered to obtain 1.47 g of the expected product after drying. 1.26 g of the product were crystallized from toluene to obtain 1.02 g of pure product (Yield: 80.2%).

| Analysis: $C_{15}H_{14}O_5$ Molecular weight = 274.27 | | |
|---|---|---|
| Calculated | C% 65.7 | H% 5.1 |
| Found | 65.4 | 5.1 |
| NMR Spectrum: $CDCl_3$ 60 MHz | | |
| H of the methyl of ester | 3.9 ppm | |
| H of the $CH_2$ of benzyl | 5.17 ppm | |
| Aromatic H's | 7.32 to 7.45 ppm | |

EXAMPLE 5

Methyl 3-(benzyloxy)-4,5-dihydroxy benzoate

Using the procedure of Example 4, the different borates of the table below were reacted. In all cases, the pure expected product was obtained with the yield indicated.

| Borate used | Yield obtained |
|---|---|
| Tripropyl borate | 81% |
| Triisopropyl borate | 97% |
| Tributyl borate | 81% |

EXAMPLE 6

Methyl 3-(allyloxy)-4,5-dihydroxy benzoate 5 g of methyl gallate and 150 ml of dimethyl formamide were mixed together under an inert gas atmosphere and then 2.46 g of sodium hydride in suspension at 53% in oil were added over 10 minutes at +15° C. After 1 hour, 4,76 ml of triethyl borate were added slowly and then 2.35 ml of allyl bromide in 50 ml of dimethyl formamide were added over 1 hour. The mixture was stirred for 2 hours at ambient temperature and then was poured into a water - ice - hydrochloric acid mixture. Extraction took place with ethyl acetate followed by washing with water, drying and evaporating to dryness. The residue was chromatographed on silica eluting with a cyclohexane - ethyl acetate (6-4) mixture to obtain 5.2 g of the expected product melting at 109° C.

| Analysis: $C_{11}H_{12}O_5$ Molecular weight = 224.216 | | |
|---|---|---|
| Calculated | C% 58.93 | H% 5.4 |
| Found | 59.2 | 5.5 |
| NMR Spectrum: $CDCl_3$ 60 MHz | | |
| H of the $CH_3$ of ester | 3.92 ppm | |
| H of the $CH_2$ of allyl | 4.63–4.72 ppm | |
| H of —CH=$CH_2$ | 5.25–6.46 ppm | |
| 2-hydroxy H's | 5.75–6.10 ppm | |
| Aromatic H's | 7.25–7.44 ppm | |

EXAMPLE 7

Methyl 3-(isopropyloxy)-4,5-dihydroxy benzoate

Using the procedure of Example 6, 1 g of methyl gallate, 0.96 ml of triethyl borate and 0.56 ml of isopropyl bromide were reacted. Another 0.56 ml of isopropyl bromide were added, followed by heating for 8 hours at 55° C. The mixture was poured into a water-ice-2N hydrochloric acid mixture, followed by extraction with ethyl acetate. The product was chromatographed on silica as in Example 6 to obtain 0.8 g of the expected product (Yield: 65%).

| Analysis: $C_{11}H_{14}O_5$ Molecular weight = 226.232 | | |
|---|---|---|
| Calculated | C% 58.4 | H% 6.24 |
| Found | 58.5 | 6.3 |
| NMR Spectrum: $CDCl_3$ 60 MHz | | |
| H of the methyls of isopropyl | 1.32–1.42 ppm | |
| H of the CH of isopropyl | 4.37–4.97 ppm | |
| H of the methyl ester | 3.9 ppm | |
| Aromatic H's | 7.23–7.37 ppm | |
| H of the 2-hydroxy H's | 5.63–6.05 ppm | |

EXAMPLE 8

Methyl 3-[methoxy-ethoxy)-methoxy]-4,5-dihydroxy benzoate

Using the procedure of Example 6, 1 g of methyl gallate, 0.96 ml of triethyl borate and 0.682 ml of (methoxy-ethoxy) methyl chloride were reacted to obtain 0.927 g of the expected product in the form of an oil after chromatography under the conditions of Example 6 (Yield: 63%).

| Analysis: $C_{12}H_{16}O_7$ Molecular weight = 272.26 | | |
|---|---|---|
| Calculated | C% 52.94 | H% 5.92 |
| Found | 53.0 | 6.3 |
| NMR Spectrum: $CDCl_3$ - 60 MHz | | |
| H of O—$CH_3$ | 3.45 | |
| H of the $CH_3$ of ester | 3.88 ppm | |
| H of the O—$CH_2$—$CH_2$—O | 3.5–4 ppm | |
| H of O—$CH_2$—O | 5.27 ppm | |
| Aromatic H's | 7.35–7.45 ppm | |

EXAMPLE 9

Methyl 3-(diphenyl-tert-butyl-silyloxy)-4,5-dihydroxy benzoate

Using the procedure of Example 6, 1 g of methyl gallate, 0.96 ml of triethyl borate and 1.482 ml of diphenyl-tert-butyl-silyl chloride were reacted to obtain 1.63 g of the expected product in the form of an oil after chromatography in the conditions of Example 6 (Yield: 71%).

| Analysis: $C_{24}H_{26}O_5Si$ Molecular weight = 422.56 | | |
|---|---|---|
| Calculated | C% 68.2 | H% 6.2 |
| Found | 69.2 | 6.4 |
| NMR Spectrum: $CDCl_3$ - 60 MHz | | |
| H of tBuSi | 1.13 ppm | |
| H of the $CH_3$ of ester | 3.63 ppm | |
| H of the 2 OH's | 5.47 ppm | |
| Aromatic H's | 6.75–7.75 ppm | |

EXAMPLE 10

Methyl 3-(pivaloyloxy)-4,5-dihydroxy benzoate

Using the procedure of Example 6, 1 g of methyl gallate, 0.96 ml of triethyl borate and 0.66 ml of pivaloyl chloride were reacted to obtain 1.07 g of the expected product in the form of an oil after chromatography on silica eluting with a cyclohexane - ethyl acetate (6-4) mixture with 1°/00 of triethylamine (Yield: 73.5%).

| Analysis: $C_{13}H_{16}O_6$ | | |
|---|---|---|
| Calculated | C% 58.2 | H% 6.0 |
| Found | 58.1 | 5.9 |
| NMR Spectrum: $CDCl_3$ - 60 MHz | | |

-continued

| | |
|---|---|
| H of tBu | 1.4 ppm |
| H of the CH₃ of ester | 3.87 ppm |
| Aromatic H's | 7.33–7.36 ppm |
| H of the OH's | 6.3 ppm |

EXAMPLE 11

Methyl 3-[(2-nitro-phenyl)-oxy]-4,5-dihyrdoxy benzoate

Using the procedure of Example 6, 5.525 g of methyl gallate, 2.72 g of sodium hydride, 5.8 ml of triethyl borate and 3.5 ml of 2-nitro fluorobenzene were tested to obtain 7.9 g of the crystallized expected product after chromatography of the crude product on silica, eluting with a cyclohexane - ethyl acetate (1-1) mixture (Yield: 86.3%).

| Analysis: $C_{14}H_{10}NO_7$ Molecular weight = 305.25 | | | |
|---|---|---|---|
| Calculated | C% 55.09 | H% 3.63 | N% 4.6 |
| Found | 55.3 | 3.6 | N% 4.6 |
| NMR Spectrum: DMSO - 250 MHz | | | |
| H of the ester | 3.78 ppm | | |
| Aromatic H's | 7.13 and 7.38 ppm, as well as 6.91 - 7.61 - 7.26 and 8.63 ppm | | |

EXAMPLE 12

1-(allyloxy)-2,3-dihydroxy benzene

A mixture of 3.8 g of pyrogallol, 76 ml of anhydrous dimethylformamide and 2.72 g of sodium hydride in suspension at 53% in oil was stirred for 3 hours under an inert gas atmosphere and then 5.27 ml of triethyl borate were added, followed by stirring for 30 minutes. Then, 2.6 ml of allyl borate in solution in 26 ml of dimethylformamide were added over 45 minutes and the mixture was stirred for 16 hours and poured into water-ice-N hydroohloric acid mixture. Extraction took place with ethyl acetate and the crude product was chromatographed on silica, eluting with a cyclohexane-ethyl acetate mixture (7-3) to obtain 3.8 g of the expected product in the form of white crystals (Yield: 76.3%).

| NMR Spectrum CDCl₃ 60 MHz. | |
|---|---|
| H of the —CH₂— of allyl | 4.58 ppm |
| H of the =CH— of allyl | 5.35 ppm |
| H of the —CH= of allyl | 6.06 ppm |
| Aromatic H's | 6.47 to 6.73 ppm |
| H of the 2 OH's | 5.53 ppm |

EXAMPLE 13

1-[(2-nitro-phenyl)-oxyl]-2,3-dihydroxy benzene 18.9 g of pyrogallol, 380 ml of anhydrous dimethylformamide and 13.6 g of sodium hydride in suspension at 53% in oil were mixed together under an inert gas atmosphere and then stirred for 45 minutes at ambient temperature. 29 ml of triethyl borate were added, and the mixture was stirred for 30 minutes. Then, 17.6 ml of 2-nitro fluorobenzene were added over one hour at 0° C. followed by stirring for 20 hours at ambient temperature. The mixture was poured into a water-ice-N hydrochloric acid mixture and the precipitate was separated, washed with petroleum ether, taken up in ethyl ether and washed with N hydrochloric ac:id to obtain about 27 g of the expected product (Yield approx.: 76%) in the form of beige crystals.

NMR Spectrum (DMSO- 250 MHz):
Aromatic H's: 6.46–6.55–6.67 to 6.74–6.81–6.91–7.16 and 7.53 ppm.

EXAMPLE 14

1-[(4-methyl-phenyl)-sulfonyloxy]-2,3-dihydroxy benzene

Using the procedure of Example 13, 18.9 g of pyrogallol, 26.3 ml of triethyl borate and 28.6 g of tosyl chloride were reacted to obtain 32 g of crude product in the form of a red resin (Yield: 76.2%).

IR Spectrum (CHCl₃):
Absorptions at 3547 cm$^{-1}$ (phenol OH's);
Absorptions at 1598–1499–1482 cm$^{-1}$ (aromatics);
Absorptions at 1365–1192–1180–1166 cm$^{-1}$ (SO₂).

EXAMPLE 15

1-(benzyloxy) 2,3-dihydroxy benzene

Using the procedure of Example 13, 25.22 g of pyrogallol, 35.1 ml of triethyl borate and 23.76 ml of benzyl bromide were reacted to obtain 33.8 g of the expected product in the form of a thick red oil after chromatography on silica eluting with a cyclohexane - ethyl acetate (6-4) mixture (Yield: 78%).

| NMR Spectrum CDCl₃ 60 MHz. | |
|---|---|
| H of benzyl CH₂ | 5.13 ppm |
| Aromatic H's | 6.5 to 7.37 ppm |
| H of the 2 OH's | 6.63 ppm |

EXAMPLE 16

1-[(4-methyl-phenyl)-sulfonyloxy]-3,4-dihydroxy benzene 1.37 g of 1,2,4-trihydroxy benzene and 40 ml of anhydrous dimethylformamide were mixed together under an inert gas atmosphere and then 0.984 g of sodium hydride in suspension at 53% in oil were added slowly at 15°–20° C. The mixture was stirred for one hour and then 1.906 ml of triethyl borate were added, followed by stirring for one hour. Then, a solution of 2.072 g of tosyl chloride in 15 ml of dimethylformamide were added over 2 hours and the mixture was stirred for 4 hours at ambient temperature. The mixture was poured into a water-ice-hydrochloric acid mixture and extraction took place with ethyl acetate followed by evaporating to dryness. The crude residue was washed with petroleum ether and after chromatography on silica and eluting with a cyclohexane-ethyl acetate (1-1) mixture, 1.53 g of the expected product were obtained which was crystallized from a flugene-isopropyl ether mixture.

| NMR Spectrum: CDCl₃ MHz | |
|---|---|
| H of the CH₃ in position 4 of phenyl | 2.47 ppm |
| Aromatic H's | 6.28 to 7.88 ppm |
| H of the 2 OH's | 6.33 ppm |

EXAMPLE 17

1-(benzyloxy)-3,4-dihydroxy benzene 1.37 g of 1,2,4-trihydroxy benzene and 30 ml of anhydrous dimethylformamide were mixed together under an inert gas atmosphere and then 0.984 g of sodium hydride in suspension at 53% in oil was added at 15°–20° C. The mixture was stirred for one hour and 1.906 ml of triethyl borate were added. The mixture was stirred for one hour, and 1.29 ml of benzyl bromide in solution in 20 ml of dimethylformamide were added over 2 hours. The mixture was stirred for 16 hours at ambient temperature and then was poured into a water-ice-N hydrochloric acid mixture. Extraction took place with ethyl acetate followed by evaporation to dryness. The residue was washed with petroleum ether, and chromatographed on silica eluting with a cyclohexane-ethyl acetate (6-4) mixture to obtain 1.36 g of the crystallized expected product (Yield: 58%).

| NMR Spectrum: CDCl$_3$ 60 MHz | |
|---|---|
| H of 20 H's | 4.57 ppm |
| H of benzyl CH$_2$ | 5.03 ppm |
| Aromatic H's | 6.37 to 7.43 ppm |

Various modifications of the process of the invention may be made without departing from the spirit or scope thereof and it is to be understood that the invention is intended to be limited only as defined in the appended claims.

What we claim is:

1. A process for the preparation of a compound of the formula

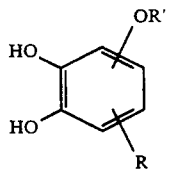

wherein R is selected from the group consisting of hydrogen, alkyl of 1 to 8 carbon atoms, alkenyl and alkynyl of 2 to 8 carbon atoms, —CN, formyl, carboxy, alkoxy carbonyl of up to 9 carbon atoms, aralkoxy carbonyl of up to 12 carbon atoms and halogen and R' is a hydroxy protective group comprising reacting a polyphenol of the formula

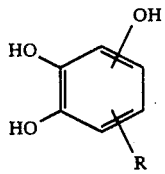

wherein R has the above definition with a base to form the corresponding dianion, reacting the latter with a trialkyl borate of the formula B(OAlk)$_3$ wherein Alk is alkyl of 1 to 6 carbon atoms to form a compound of the formula alk O—B(O)(O)—[aromatic ring with OH and R]   III reacting the latter with a reagent capable of introducing a hydroxy protective group and reacting the latter with a hydrolysis agent for the oxygen-boron bond to obtain the corresponding compound of Formula I.

2. The process of claim 1 wherein at least two equivalents of sodium hydride or lithium alkyl are used as the base.

3. The process of claim 2 wherein the base is sodium hydride.

4. The process of claim 1 wherein the reaction with trialkyl borate is effected in an aprotic organic solvent.

5. The process of claim 4 wherein the solvent is tetrahydrofuran or dimethylformamide.

6. The process of claim 1 wherein Alk is selected from the group consisting of methyl, ethyl, propyl, isopropyl and butyl.

7. The process of claim 1 wherein the steps are effected at room temperature.

8. The process of claim 1 wherein the hydrolysis agent is an acid or an oxidizing agent.

9. The process of claim 1 wherein the hydrolysis agent is hydrochloric acid.

* * * * *